US010076452B2

(12) United States Patent
Jorgensen et al.

(10) Patent No.: US 10,076,452 B2
(45) Date of Patent: Sep. 18, 2018

(54) TAMPON PLEDGET FOR INCREASED BYPASS LEAKAGE PROTECTION

(71) Applicant: Edgewell Personal Care Brands, LLC, Chesterfield, MO (US)

(72) Inventors: Robert Jorgensen, Middletown, DE (US); Keith Edgett, Middletown, DE (US)

(73) Assignee: Edgewell Personal Care Brands, LLC., Chesterfield, MO (US)

( * ) Notice: Subject to any disclaimer, the term of this patent is extended or adjusted under 35 U.S.C. 154(b) by 405 days.

(21) Appl. No.: 14/972,442

(22) Filed: Dec. 17, 2015

(65) Prior Publication Data

US 2016/0100993 A1    Apr. 14, 2016

Related U.S. Application Data

(63) Continuation of application No. 12/958,897, filed on Dec. 2, 2010, now Pat. No. 9,259,360, which is a (Continued)

(51) Int. Cl.
| | |
|---|---|
| *A61F 13/20* | (2006.01) |
| *A61F 13/15* | (2006.01) |
| *A61L 15/28* | (2006.01) |
| *A61L 15/42* | (2006.01) |
| *A61L 15/60* | (2006.01) |

(52) U.S. Cl.
CPC ...... *A61F 13/208* (2013.01); *A61F 13/15203* (2013.01); *A61F 13/2025* (2013.01); *A61F 13/2028* (2013.01); *A61F 13/2057* (2013.01); *A61F 13/2065* (2013.01); *A61F 13/2068* (2013.01); *A61F 13/2088* (2013.01);
(Continued)

(58) Field of Classification Search
CPC .............. A61F 13/2088; A61F 13/2082; A61F 13/2094; A61F 13/2085; A61F 13/2091; A61F 13/2097; A61F 13/2054; A61F 13/2062; A61F 13/2065; A61F 13/2068; A61F 13/15699; A61F 13/15707; A61F 13/15747; A61F 13/208; A61F 13/2028
USPC ........................................... 28/118, 119, 120
See application file for complete search history.

(56) References Cited

U.S. PATENT DOCUMENTS

| | | |
|---|---|---|
| 1,401,358 A | 12/1921 | Peterkin |
| 2,330,257 A | 9/1943 | Bailey |
| | (Continued) | |

FOREIGN PATENT DOCUMENTS

| | | |
|---|---|---|
| BE | 768046 A | 11/1971 |
| CA | 2127144 A1 | 10/1995 |
| | (Continued) | |

OTHER PUBLICATIONS

Playtex Beyond tampon (2005).
(Continued)

*Primary Examiner* — Amy Vanatta (57) ABSTRACT

There is provided a tampon pledget that includes one or more enhanced features that result in the pledget exhibiting increased bypass leakage prevention. These enhanced features may include, but are not limited to, geometry, absorption, and any combinations thereof. There is also provided one or more methods for constructing a tampon pledget having increased bypass leakage protection.

38 Claims, 3 Drawing Sheets

Related U.S. Application Data continuation of application No. 11/983,264, filed on Nov. 8, 2007, now Pat. No. 7,867,209.

(60) Provisional application No. 60/857,694, filed on Nov. 8, 2006.

(52) U.S. Cl.
CPC ............ *A61L 15/28* (2013.01); *A61L 15/425* (2013.01); *A61L 15/60* (2013.01); *A61F 2013/15447* (2013.01)

(56) References Cited

U.S. PATENT DOCUMENTS

| | | | |
|---|---|---|---|
| 2,391,343 A | 12/1945 | Popper | |
| 2,412,861 A | 12/1946 | George et al. | |
| 2,425,004 A * | 8/1947 | Rabell | A61F 13/2085 264/258 |
| 2,433,675 A * | 12/1947 | Parish | A61F 13/2085 264/134 |
| 2,455,925 A * | 12/1948 | Ganz | A61F 13/2085 28/119 |
| 2,495,420 A * | 1/1950 | Popper | A61F 13/2085 264/257 |
| 2,499,414 A | 3/1950 | Rabell | |
| 2,761,449 A | 9/1956 | Bletzinger | |
| 3,051,177 A | 8/1962 | Wilson | |
| 3,079,921 A | 3/1963 | Brecht et al. | |
| 3,320,956 A | 5/1967 | Steiger | |
| 3,340,874 A | 9/1967 | Burgeni | |
| 3,371,666 A | 3/1968 | Lewing | |
| 3,397,695 A | 8/1968 | Voss | |
| 3,409,011 A | 11/1968 | Mittag | |
| 3,465,390 A | 9/1969 | Mooney | |
| 3,572,341 A | 3/1971 | Glassman | |
| 3,606,643 A | 9/1971 | Mooney | |
| 3,610,243 A | 10/1971 | Jones, Sr. | |
| 3,618,605 A | 11/1971 | Glassman | |
| 3,628,534 A | 12/1971 | Donohue | |
| 3,643,661 A | 2/1972 | Crockford | |
| 3,674,026 A | 7/1972 | Werner et al. | |
| 3,683,912 A | 8/1972 | Olsen et al. | |
| 3,695,270 A | 10/1972 | Dostal | |
| 3,699,962 A | 10/1972 | Hanke | |
| 3,699,965 A | 10/1972 | Dostal | |
| 3,712,305 A | 1/1973 | Wennerblom et al. | |
| 3,731,687 A | 5/1973 | Glassman | |
| RE27,677 E | 6/1973 | Glassman | |
| 3,738,364 A | 6/1973 | Brien et al. | |
| 3,749,094 A | 7/1973 | Duncan | |
| 3,805,786 A | 4/1974 | Bernardin et al. | |
| 3,811,445 A | 5/1974 | Dostal | |
| 3,834,389 A | 9/1974 | Dulle | |
| 3,854,481 A * | 12/1974 | Messing | A61F 13/206 428/40.1 |
| 3,981,305 A | 9/1976 | Ring | |
| 4,200,101 A | 4/1980 | Glassman | |
| 4,212,301 A | 7/1980 | Johnson | |
| 4,274,412 A | 6/1981 | Austin | |
| 4,318,407 A | 3/1982 | Woon | |
| 4,326,527 A * | 4/1982 | Wollangk | A61F 13/2085 28/118 |
| 4,335,720 A | 6/1982 | Glassman | |
| 4,335,721 A | 6/1982 | Mathews | |
| 4,373,529 A | 2/1983 | Lilaonitkul et al. | |
| 4,374,522 A | 2/1983 | Olevsky | |
| 4,543,098 A | 9/1985 | Wolfe | |
| 4,627,849 A | 12/1986 | Walton | |
| 4,787,895 A | 11/1988 | Stokes et al. | |
| 4,835,042 A * | 5/1989 | Dohzono | A61F 13/2051 264/517 |
| 4,836,587 A | 6/1989 | Hinzmann | |
| 4,857,044 A | 8/1989 | Lennon | |
| 4,973,302 A | 11/1990 | Armour et al. | |
| 5,004,467 A | 4/1991 | Hinzmann et al. | |
| 5,006,116 A | 4/1991 | Alikhan et al. | |
| 5,047,024 A | 9/1991 | Glassman | |
| 5,112,348 A | 5/1992 | Glassman | |
| 5,149,332 A | 9/1992 | Walton | |
| 5,153,971 A | 10/1992 | Van Iten | |
| 5,314,743 A | 5/1994 | Meirowitz et al. | |
| 5,364,383 A | 11/1994 | Hayes et al. | |
| 5,389,067 A | 2/1995 | Rejai | |
| 5,443,776 A | 8/1995 | Bartholomew et al. | |
| 5,471,820 A | 12/1995 | Oppe et al. | |
| 5,634,248 A | 6/1997 | McNelis et al. | |
| 5,659,934 A | 8/1997 | Jessup et al. | |
| 5,681,894 A | 10/1997 | Williams et al. | |
| 5,755,906 A | 5/1998 | Achter et al. | |
| 5,788,910 A | 8/1998 | McNelis et al. | |
| 5,795,346 A | 8/1998 | Achter et al. | |
| 5,804,653 A | 9/1998 | Weng | |
| 5,807,372 A | 9/1998 | Balzar | |
| 5,827,256 A | 10/1998 | Balzar | |
| 5,873,971 A | 2/1999 | Balzar | |
| 5,891,081 A | 4/1999 | McNelis et al. | |
| 5,891,123 A | 4/1999 | Balzar | |
| 5,931,803 A | 8/1999 | Jackson | |
| 5,986,000 A | 11/1999 | Williams et al. | |
| 6,003,216 A * | 12/1999 | Hull, Jr. | A61F 13/2085 28/118 |
| 6,019,744 A | 2/2000 | Altdorf et al. | |
| 6,039,716 A | 3/2000 | Jessup et al. | |
| 6,039,828 A | 3/2000 | Achter et al. | |
| 6,045,526 A | 4/2000 | Jackson | |
| 6,142,984 A | 11/2000 | Brown et al. | |
| 6,177,608 B1 | 1/2001 | Weinstrauch | |
| 6,179,802 B1 | 1/2001 | Jackson | |
| 6,183,436 B1 | 2/2001 | Korteweg et al. | |
| 6,186,994 B1 | 2/2001 | Bowles et al. | |
| 6,186,995 B1 | 2/2001 | Tharpe, Jr. | |
| 6,248,274 B1 | 6/2001 | Williams | |
| 6,283,952 B1 * | 9/2001 | Child | A61F 13/2051 28/118 |
| 6,315,763 B1 | 11/2001 | Albright et al. | |
| 6,333,108 B1 | 12/2001 | Wilkes et al. | |
| 6,353,146 B1 | 3/2002 | Williams | |
| 6,419,777 B1 | 7/2002 | Achter et al. | |
| 6,478,726 B1 | 11/2002 | Zunker | |
| 6,506,958 B2 | 1/2003 | Williams | |
| 6,511,452 B1 | 1/2003 | Rejai et al. | |
| 6,558,370 B2 | 5/2003 | Moser | |
| 6,585,300 B2 | 7/2003 | Rajala et al. | |
| 6,595,974 B1 | 7/2003 | Pauley et al. | |
| 6,596,919 B2 | 7/2003 | Williams | |
| 6,603,054 B2 | 8/2003 | Chen et al. | |
| 6,635,205 B2 | 10/2003 | Williams et al. | |
| 6,635,800 B2 | 10/2003 | Jackson et al. | |
| 6,682,513 B2 | 1/2004 | Agyapong et al. | |
| 6,702,797 B2 | 3/2004 | Williams | |
| 6,719,743 B1 | 4/2004 | Wada | |
| 6,740,070 B2 | 5/2004 | Agyapong et al. | |
| D492,033 S | 6/2004 | Jarmon et al. | |
| 6,746,418 B1 | 6/2004 | Pauley et al. | |
| 6,814,722 B2 | 11/2004 | Jackson et al. | |
| 6,830,554 B2 | 12/2004 | Jackson et al. | |
| 6,886,443 B2 | 5/2005 | Rejai | |
| 6,887,226 B2 | 5/2005 | Cassoni et al. | |
| 6,890,324 B1 | 5/2005 | Jackson et al. | |
| 6,923,789 B2 | 8/2005 | LeMay et al. | |
| 6,932,805 B2 | 8/2005 | Domeier et al. | |
| 6,953,456 B2 | 10/2005 | Fuchs et al. | |
| 7,044,928 B2 | 5/2006 | LeMay et al. | |
| 7,160,279 B2 | 1/2007 | Pauley et al. | |
| 7,226,436 B2 | 6/2007 | Gorham et al. | |
| 7,244,497 B2 | 7/2007 | Hartmann et al. | |
| 7,250,129 B2 | 7/2007 | Williams et al. | |
| 7,335,194 B2 | 2/2008 | Wada | |
| 7,387,622 B1 | 6/2008 | Pauley et al. | |
| D572,362 S | 7/2008 | Edgett et al. | |
| 7,416,997 B2 | 8/2008 | Kim et al. | |
| D579,113 S | 10/2008 | Edgett et al. | |
| 7,563,401 B2 | 7/2009 | Pham et al. | |

(56) References Cited

U.S. PATENT DOCUMENTS

| | | |
|---|---|---|
| 7,579,078 B2 | 8/2009 | Hartmann et al. |
| D612,940 S | 3/2010 | Edgett et al. |
| 7,678,095 B2 | 3/2010 | Jackson et al. |
| 7,704,242 B2 | 4/2010 | LeMay et al. |
| 7,727,208 B2 | 6/2010 | Lemay et al. |
| 7,727,210 B2 | 6/2010 | LeMay et al. |
| 7,745,686 B2 | 6/2010 | Mauro et al. |
| 7,780,892 B2 | 8/2010 | Miller et al. |
| 7,798,986 B2 | 9/2010 | Melvin et al. |
| 7,799,966 B2 | 9/2010 | Williams et al. |
| 7,815,594 B2 | 10/2010 | Dougherty, Jr. et al. |
| D626,650 S | 11/2010 | Edgett et al. |
| 7,862,533 B2 | 1/2011 | LeMay et al. |
| 7,867,209 B2 | 1/2011 | Jorgensen et al. |
| 7,887,525 B2 | 2/2011 | Gorham et al. |
| 8,070,710 B2 | 12/2011 | Dougherty, Jr. |
| 8,093,446 B2 | 1/2012 | Knuth et al. |
| 8,166,834 B2 | 5/2012 | Dougherty, Jr. et al. |
| 8,197,434 B2 | 6/2012 | LeMay et al. |
| 8,198,504 B2 | 6/2012 | Glaug et al. |
| 8,221,375 B2 | 7/2012 | LeMay et al. |
| 8,323,256 B2 | 12/2012 | Edgett et al. |
| 8,372,027 B2 | 2/2013 | LeMay et al. |
| 8,444,590 B2 | 5/2013 | LeMay et al. |
| 8,556,845 B2 | 10/2013 | Lemay et al. |
| 8,571,883 B2 | 10/2013 | Dougherty, Jr. et al. |
| 8,585,668 B2 | 11/2013 | Pauley et al. |
| 8,696,957 B2 | 4/2014 | Dougherty, Jr. et al. |
| 8,735,647 B2 | 5/2014 | Schoelling |
| 8,827,974 B2 | 9/2014 | Schmidt-Forst |
| 8,961,449 B2 | 2/2015 | Jorgensen et al. |
| 9,107,775 B2 | 8/2015 | Edgett et al. |
| 9,125,771 B2 | 9/2015 | Schoelling |
| 9,173,778 B2 | 11/2015 | Schoelling |
| 9,192,522 B2 | 11/2015 | Edgett et al. |
| 2002/0107494 A1 | 8/2002 | Williams |
| 2002/0120243 A1 | 8/2002 | Kraemer et al. |
| 2002/0128620 A1 | 9/2002 | Jackson et al. |
| 2002/0156442 A1 | 10/2002 | Jackson et al. |
| 2003/0131456 A1 | 7/2003 | Rajala et al. |
| 2003/0149416 A1 | 8/2003 | Cole et al. |
| 2003/0158533 A1 | 8/2003 | Agyapong et al. |
| 2003/0172504 A1* | 9/2003 | Sageser ............... A61F 13/2085 28/118 |
| 2003/0208180 A1 | 11/2003 | Fuchs et al. |
| 2003/0225389 A1 | 12/2003 | Cassoni et al. |
| 2003/0236499 A1 | 12/2003 | Fedyk et al. |
| 2004/0019317 A1 | 1/2004 | Takagi et al. |
| 2004/0126555 A1 | 7/2004 | Hartmann et al. |
| 2004/0019313 A1 | 9/2004 | Wada |
| 2004/0193131 A1 | 9/2004 | Wada |
| 2005/0059944 A1 | 3/2005 | Jackson et al. |
| 2005/0096619 A1 | 5/2005 | Costa |
| 2007/0026228 A1 | 2/2007 | Hartmann et al. |
| 2007/0234532 A1* | 10/2007 | Gilbert ............... A61F 13/2051 28/118 |
| 2007/0260211 A1 | 11/2007 | Schmidt-Forst |
| 2008/0065041 A1 | 3/2008 | Stan et al. |
| 2008/0097366 A1 | 4/2008 | Matthews |
| 2008/0110005 A1 | 5/2008 | Gilbert et al. |
| 2008/0119811 A1 | 5/2008 | Gilbert et al. |
| 2008/0281514 A1 | 5/2008 | Dougherty, Jr. et al. |
| 2008/0221502 A1 | 9/2008 | Binner et al. |
| 2008/0262464 A1 | 10/2008 | Hasse et al. |
| 2008/0287902 A1 | 11/2008 | Edgett et al. |
| 2009/0036859 A1 | 2/2009 | Dougherty, Jr. et al. |
| 2009/0082712 A1 | 3/2009 | Hasse et al. |
| 2009/0234268 A1 | 3/2009 | Jorgensen et al. |
| 2009/0156979 A1 | 6/2009 | Andersch |
| 2009/0227975 A1 | 9/2009 | Dougherty, Jr. et al. |
| 2009/0247981 A1 | 10/2009 | Glaug et al. |
| 2009/0281474 A1 | 11/2009 | Dougherty, Jr. et al. |
| 2010/0036309 A1 | 2/2010 | Jorgensen, Jr. et al. |
| 2010/0056981 A1 | 3/2010 | Karapasha et al. |
| 2010/0120707 A1 | 5/2010 | Dougherty, Jr. et al. |
| 2010/0160886 A1 | 6/2010 | Jackson et al. |
| 2010/0198133 A1 | 8/2010 | Dougherty, Jr. et al. |
| 2011/0224637 A1 | 9/2011 | Edgett et al. |
| 2012/0061867 A1 | 3/2012 | Dougherty, Jr. et al. |
| 2013/0018347 A1 | 1/2013 | Edgett et al. |
| 2014/0265026 A1 | 9/2014 | Schoelling |
| 2014/0276523 A1 | 9/2014 | Schoelling |
| 2015/0105711 A1 | 4/2015 | LeMay et al. |
| 2015/0320608 A1 | 7/2015 | Edgett et al. |

FOREIGN PATENT DOCUMENTS

| | | |
|---|---|---|
| CA | 2441647 A1 | 5/1996 |
| CA | 2180789 A1 | 1/1997 |
| CA | 2312666 A1 | 1/2001 |
| CA | 108982 S | 8/2006 |
| CA | 115880 S | 8/2008 |
| FR | 2207687 | 6/1974 |
| FR | 2505176 A | 11/1982 |
| GB | 1108197 A | 4/1968 |
| GB | 2073592 | 10/1981 |
| GB | 9306074 A | 5/1993 |
| IE | 8904080 A | 6/1990 |
| IL | 109027 | 6/1994 |
| JP | SHO44004240 | 2/1944 |
| JP | 62-8754 | 1/1987 |
| JP | 63-212358 | 9/1988 |
| JP | H05-68695 | 3/1993 |
| JP | 2001-008964 | 1/2001 |
| JP | 2005-526584 | 9/2005 |
| JP | SHO62-027952 | 9/2005 |
| WO | WO9933428 A1 | 7/1999 |
| WO | WO0006071 A1 | 2/2000 |
| WO | WO0124729 A1 | 4/2001 |
| WO | WO0166055 A1 | 9/2001 |
| WO | WO02058587 A1 | 8/2002 |
| WO | WO2003101362 A2 | 11/2003 |
| WO | WO2005041883 A1 | 5/2005 |
| WO | WO2005112856 A1 | 12/2005 |
| WO | WO2005112862 A1 | 12/2005 |
| WO | WO2006016933 A1 | 2/2006 |
| WO | WO2007078413 A1 | 2/2007 |
| WO | WO 2007/078413 | 7/2007 |
| WO | WO2008056339 A1 | 5/2008 |
| WO | WO200809331 A1 | 8/2008 |
| WO | WO2008144624 A1 | 11/2008 |
| ZA | 8803191 | 11/1988 |
| ZA | 9706745 | 2/1998 |

OTHER PUBLICATIONS

Playtex Gentle Glide tampon (2005).
Examination Report for corresponding GB Application No. GB1117582.5, dated Mar. 27, 2013, pp. 1-2.
English Translation of Decision of Rejection against Japanese Patent Application No. 2012-506079; dated Jan. 7, 2013; pp. 1-4.
International Search Report for PCT/US2010/030351 dated Jun. 3, 2010.
PCT International Search Report, International Application No. PCT/US2008/064074, International Filing Date May 19, 2008, dated Jul. 21, 2008.
First Office Action Against JP Application No. 2010-508629, dated Dec. 20, 2011.
International Search Report dated Jun. 2, 2008, for International application No. PCT/*S07/13749.
Written Opinion dated Jun. 2, 2008, for International application No. PCT/US07/13749.
English Translation of Decision of Rejection against Japanese Patent Application No. 2010-508629; dated Dec. 27, 2012; pp. 1-3.
First Office Action dated Feb. 13, 2012 from Japanese Application No. 2009-536296.
Korean Office Action dated Dec. 16, 2011 from Korean Application No. 10-2009-7011433.
First Office Action dated Feb. 13, 2012, from Japanese Application No. 2009-536296.

(56) References Cited

OTHER PUBLICATIONS

Supplemental European Search Report dated Aug. 5, 2011, from European Application No. 07839986.2.
Office Action dated Apr. 11, 2011 for corresponding Korean Patent Application No. 10-2009-7011433 with English summary of Office Action.
Examination Report for Canadian Patent Application No. 2669469 dated Dec. 1, 2010.
2005 Gentle Glide Plastic Tampons.

* cited by examiner

TAMPON PLEDGET FOR INCREASED BYPASS LEAKAGE PROTECTION

CROSS-REFERENCE TO RELATED APPLICATIONS

This is a continuation application of U.S. patent application Ser. No. 12/958,897 filed Dec. 2, 2010, which is a continuation application of U.S. patent application Ser. No. 11/983,264, filed Nov. 8, 2007, which claims the benefit of priority from U.S. Provisional patent application Ser. No. 60/857,694, filed on 8 Nov. 2006. Each of the above-noted applications is incorporated herein by reference.

BACKGROUND OF THE INVENTION

A. Field of Endeavor

The present disclosure relates generally to tampon pledgets. More particularly, the present disclosure relates to tampon pledgets that exhibit increased bypass leakage protection.

B. Description of the Prior Art

Both in-vivo and in-vitro testing has shown that current tampon pledgets do not protect well against bypass leakage. In-vivo testing shows that the typical woman places the tampon pledget too deep into the vaginal canal and is not optimally placed to absorb fluid. In-vitro testing confirms that tampon pledget expansion is not optimal. With both of these insights, it is known that there is a propensity for the tampon pledgets to leak prematurely, i.e., bypass leakage.

There have been many attempts in the prior art to address bypass leakage. Examples include providing a tampon pledget with various pre-expanded, compressed shapes designed to conform to a user's anatomy upon insertion into the vagina. One particular drawback with the tampon pledget having a pre-expanded shape is that it may be difficult to house the pre-shaped pledget in a typical cylindrical applicator barrel due to its shape. Also, once housed in the applicator, the tampon pledget having the pre-expanded shape may exert additional forces on the walls of the applicator barrel due to its shape, which in turn could cause excess friction during expulsion, requiring additional force to expel the tampon pledget from the applicator. The required additional force could make use of the applicator difficult, and in some cases actually cause deformation of the applicator, making its use extremely difficult.

Therefore, there remains a need in the tampon art for a tampon pledget that mitigates or all together prevents bypass leakage, while also avoiding the drawbacks associated with the prior art. The present disclosure meets this need.

SUMMARY OF THE INVENTION

The present disclosure provides a tampon pledget that exhibits increased bypass leakage prevention.

The present disclosure also provides such a tampon pledget that has increased absorption potential at a base of the pledget.

The present disclosure further provides such a tampon pledget that has increased expansion potential at the base of the pledget.

The present disclosure still further provides such a tampon pledget where the desired pledget geometry occurs post-expansion.

The present disclosure yet further provides such a tampon pledget with varying fiber weight distribution across the length and/or width of the pledget.

The present disclosure also provides a method for assembling a tampon pledget that exhibits increased bypass leakage prevention.

These and other advantages and benefits of the present disclosure are provided by a tampon pledget that includes one or more enhanced features that result in the pledget exhibiting increased bypass leakage prevention. These enhanced features may include, but are not limited to, geometry, absorption, or any combinations thereof. The present disclosure also provides one or more methods for constructing a tampon pledget having increased bypass leakage protection.

DETAILED DESCRIPTION OF THE INVENTION

The present disclosure provides a unique tampon pledget designed for various tampon sorts with one or more enhanced features including, but not limited to, increased absorption potential at the base of the pledget, increased expansion potential at the base of the pledget, and any combinations thereof. These enhanced features are achieved by constructing the tampon pledget with certain pad lay-up ratios, fiber weight distribution ratios, and any combinations thereof. As a result of these one or more enhanced features, a tampon pledget having increased bypass leakage protection results. Additionally, the enhanced features do not compromise the desired pledget geometry, or its pre-expansion ability. Therefore, applicator modifications are not required to house the tampon pledget of the present disclosure.

Figure 1:
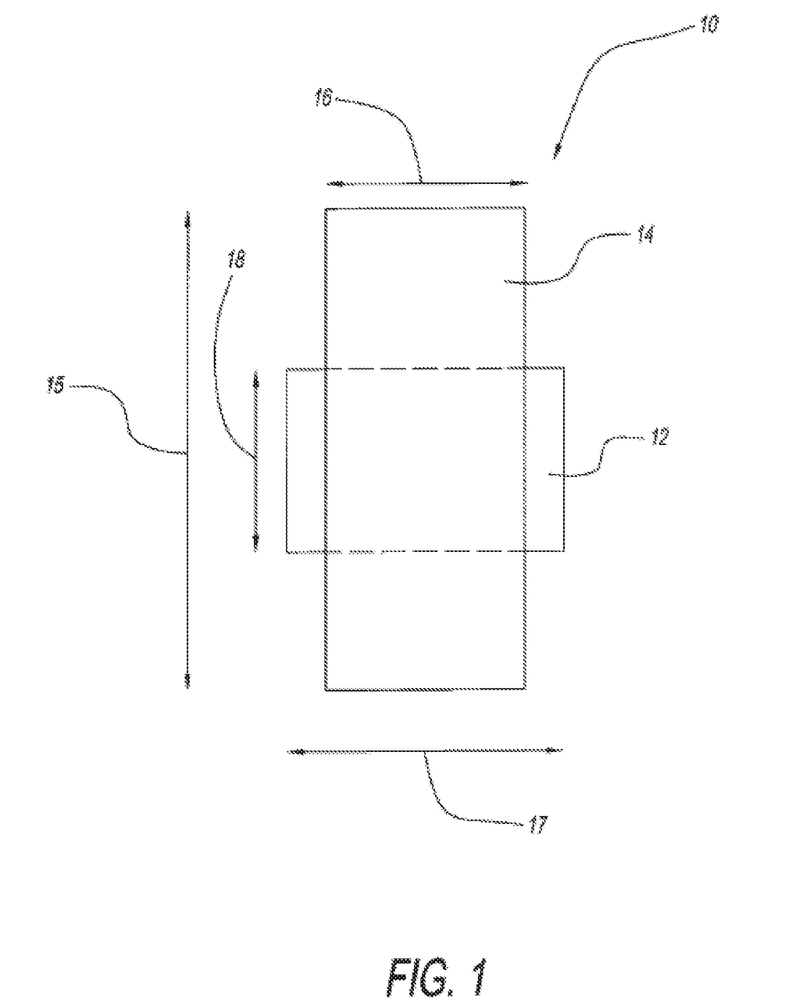
FIG. 1 is top view of pads positioned for a tampon pledget prior to formation of the tampon pledget according to the present disclosure.

The present disclosure provides a unique tampon pledget designed for various tampon sorts with one or more enhanced features including, but not limited to, increased absorption potential at the base of the pledget, increased expansion potential at the base of the pledget, and any combinations thereof. These enhanced features are achieved by constructing the tampon pledget with certain pad lay-up ratios, fiber weight distribution ratios, and any combinations thereof. As a result of these one or more enhanced features, a tampon pledget having increased bypass leakage protection results. Additionally, the enhanced features do not compromise the desired pledget geometry, or its pre-expansion ability. Therefore, applicator modifications are not required to house the tampon pledget of the present disclosure.

to FIG. 1, the present disclosure is exemplified by the pad lay-up represented generally by reference numeral 10. Pad lay-up 10 includes one or more bottom pads 12 and one or more top pads 14. While pad lay-up 10 depicts the one or more bottom pads 12 and one or more top pads 14 in a cross-pad configuration, it should be understood that the pad lay-up can be configured in any suitable shape, including, but not limited to cross, chevron, diamond, circular, oval, square, rectangle, and any combinations thereof.

It has been unexpectedly found that by providing one or more bottom pads 12 with one or more top pads 14 in certain pad lay-up ratios, and based on their respective areas, various desirable tampon pledget configurations can be achieved that provide enhanced bypass leakage protection. Area is defined herein as length times width (without depth as a factor). The pad lay-up ratio is defined as the ratio of the area of one or more bottom pads 12 to the area of one or more top pads 14, with the area of the one or more pads calculated in a single plane. Therefore, while stacking of multiple pads may be done, it does not increase the calculated area of the one or more pads.

Again referring to FIG. 1, the one or more top pads 14 each has a length dimension 15 and a width dimension 16. The one or more bottom pads 12 each have a length dimension 17 and a width dimension 18.

In one embodiment, the one or more top pads 14 each have a length dimension 15 between about 2 inches and about 6 inches. In another embodiment, the one or more top pads 14 each have a length between about 3.5 inches and about 5.0 inches. In yet another embodiment, the one or more top pads 14 each has a length about 4 inches.

In one embodiment, the one or more top pads 14 each have a width dimension 16 between about 1 inches and about 4 inches. In another embodiment, the one or more top pads 14 each have a width between about 1.5 inches and about 3 inches. In yet another embodiment, the one or more top pads 14 each has a width about 2 inches.

In one embodiment, the one or more bottom pads 12 each have a length dimension 17 between about 1 inch and about 4 inches. In another embodiment, the one or more bottom pads 12 each have a length between about 2 inches and about 3 inches. In yet another embodiment, the one or more bottom pads 12 each have a length about 2.5 inches.

In one embodiment, the one or more bottom pads 12 each have a width dimension 18 between about 1 inch and about 4 inches. In another embodiment, the one or more bottom pads 12 each have a width between about 1.5 inches and about 3 inches. In yet another embodiment, the one or more bottom pads 12 each have a width about 2 inches.

In one embodiment of the present disclosure, the pad lay-up ratio is between about 1:1.2 to about 1:2.25. In another embodiment of the present invention, the pad lay-up ratio is about 1:1.6.

Another important aspect of the present disclosure is the fiber weight distribution ratio between the one or more bottom pads 12 and the one or more top pads 14. The fiber weight distribution ratio is defined as the ratio of the fiber weight distribution of the one or more bottom pads 12 to the fiber weight distribution of the one or more top pads 14.

In one embodiment according to the present disclosure, the fiber weight distribution ratio is between about 0.5:1 to about 2:1. In another embodiment according to the present disclosure, the fiber weight distribution ratio is between about 0.75:1 to about 1.5:1. In yet another embodiment according to the present disclosure, the fiber weight distribution ratio is about 1:1.

Suitable materials for use in forming the one or more bottom pads and/or the one or more top pads include, but are not limited to, cellulosic, rayon, cotton, pulp, superabsorbent, absorbent foam, and any combinations thereof.

The tampon pledget may include a liquid permeable coverstock or overwrap material, if desired. Suitable coverstock materials may include, but are not limited to, rayon, cotton, bicomponent fiber, or other suitable natural or synthetic fibers known in the art. Rayon, polyethylene, polypropylene and blends of these are particularly suited for use as a coverstock material.

The following examples demonstrate various embodiments according to the present disclosure. These examples are not intended to limit the scope of the present disclosure.

The pledget shape after exposure to moisture can vary according to the ratios set forth above in accordance with the present disclosure.

Example 1

Figure 2:
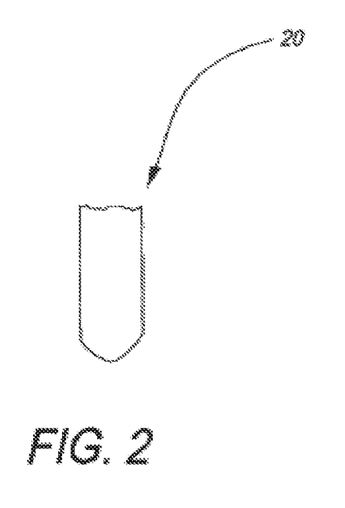
FIG. 2 is a side view of one embodiment of a formed tampon pledget according to the present disclosure.

A tampon pledget 20 with a pad lay-up ratio of about 1:1.2 and fiber distribution ratio of about 0.75:1 may be constructed. Referring to FIG. 2, tampon pledget 20 with these ratios will have straight wall sides to a slight teardrop or circular shape.

Example 2

Figure 3:
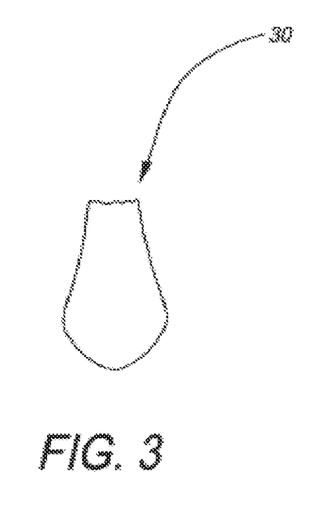
FIG. 3 is a side view of another embodiment of a formed tampon pledget according to the present disclosure.

A tampon pledget 30 with a pad lay-up ratio of about 1:2.25 and fiber distribution ratio of about 1.5:1 may be constructed. Referring to FIG. 3, tampon pledget 30 with these ratios will have a teardrop shape.

Example 3

Figure 4:
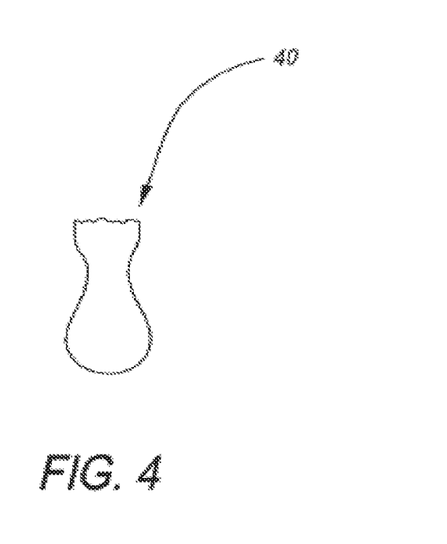
FIG. 4 is a side view of yet another embodiment of a formed tampon pledget according to the present disclosure.

A tampon pledget 40 with a pad lay-up ratio of about 1:1.6 and fiber distribution ratio of about 1:1 may be constructed. Referring to FIG. 4, tampon pledget 40 with these ratios will have a step-down multi-tiered to teardrop shape.

Comparative Examples 4 Through 6

Several commercial tampon pledgets were purchased from retail stores to be used as comparative examples used to compare with tampon pledgets of this present disclosure. Comparative Example 4 tampons or tampon pledgets are Tampax Original (Super) tampons (available from Procter & Gamble); Comparative Example 5 tampons are Tampax Pearl (Super) Unscented tampons (available from Procter & Gamble); and Comparative Example 6 tampons are Kotex Security Super tampons (available from Kimberly Clark).

Example 7

Figure 5:
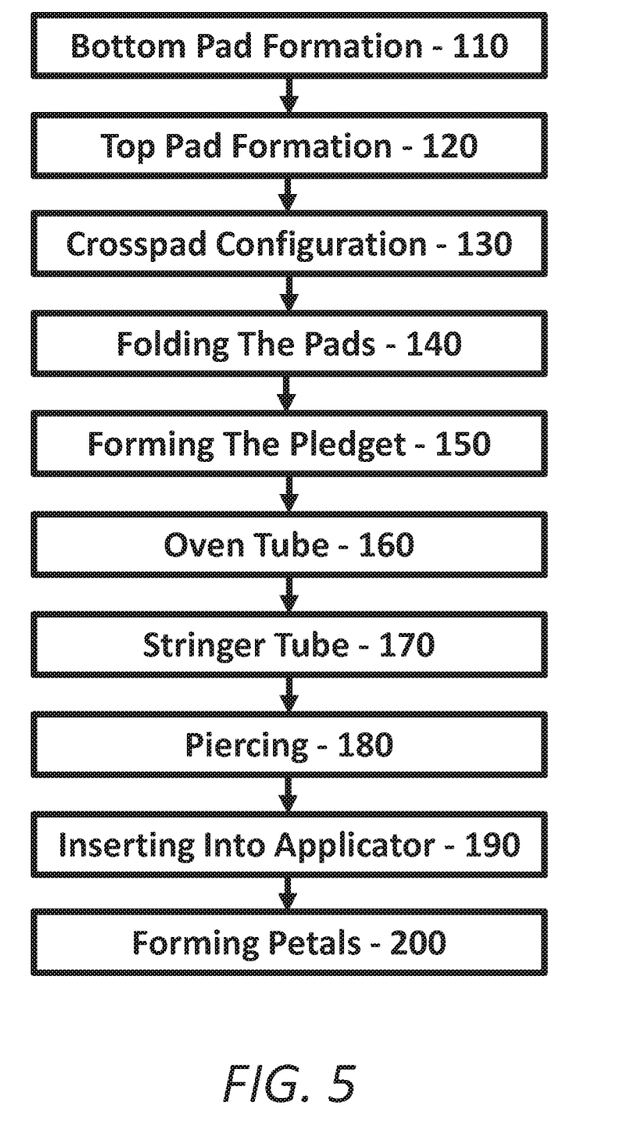
FIG. 5 is a process flow chart for an embodiment of a method of manufacturing according to the present disclosure.

Referring to FIG. 5, approximately 60 tampon pledgets were constructed according to the present disclosure invention and tested. These are similar to those described in Example 1. These tampon pledgets were constructed with a pad lay-up ratio of about 1:1.25 and a fiber distribution ratio of about 1:1. Specifically, a bottom pad (2.25"×2.5" from one Galaxy-based web) 110 and a top pad (4"×1.75" of a second Galaxy-based web) 120 were used to construct these tampon pledgets. The top (or inside) pad moisture, as measured by a Halogen Moisture analyzer (Mettler-Toledo) was about 9.78%. The bottom (or outside) pad moisture was 11.55%. Tampon pledget weights were 2.60 g (average)+/− 0.03 g (one standard deviation). The tampon pledgets were all constructed as outlined herein, according to the present disclosure.

To form the tampon pledgets of the above Examples, individual pads 110, 120 were arranged in a crosspad configuration according to the present disclosure invention and carefully weighed 130. Using a Hauni machine, the crosspad tampon pledget 130 was delivered and folded 140, using an appropriately sized (about 0.25") fluted ram, into a cylindrical shaped transfer tube to form a cylindrical tampon pledget 150. The pledget was then transferred again using another ram into a warmed oven tube (inside diameter about 0.5", temperature about 220° F.) and then conveyed by a pre-heated IR conveyor oven (Infrared Heating Technologies, LLC) 160. This heated, compressed cylindrical tampon pledget was then transferred into a slightly larger diameter stringer tube 170. In this tube, a needle was pierced through to permit a Nalan-coated string to be added and tied 180. Following the addition of string, the tampon pledget was added to a standard Gentle Glide™ plastic applicator 190. The petals on the applicator were then heated to about 190° F. and shaped, to "close" them 200. These finished tampon pledgets were stored for at least one day. Then testing, as outlined above, was performed.

Syngyna absorbency was evaluated according to the usual FDA mandated testing procedure, as outlined in the Federal Register, Part 801, 801.430. The Syngyna absorbency, measured for 20 such tampon pledgets, was 10.93+/−0.29 grams, consistent with a super absorbency tampon pledget.

A modified syngyna absorbency test, known as the positive displacement test, was performed. In this modification of the usual FDA procedure, instead of circulating the 27° C. water continuously inside the tube around the condom that encases the tampon pledget, the water was directed to a burette, which was located three inches higher than the top of the syngyna tube. The water level in this burette was adjusted to the zero level at the start of the syngyna experiment. Then, as the tampon pledget expanded to form a shape similar to the teardrop shape of FIG. 3, the water level in the tube increased. This increase was monitored every thirty seconds.

The purpose of this test was to see how rapidly the volume of the tampon pledget expanded during a syngyna absorbency experiment and to compare these results with those for comparable commercial tampon pledgets set forth in Comparative Examples 4 through 6.

Table 1 below provides these results. Twenty tampon pledgets for each of these examples were tested using the procedure outlined above. Since tampon pledget weights vary slightly from manufacturer to manufacturer, Table 1 reports normalized slopes; that is, the rate of volumetric increase vs. time was divided by the average pledget weights, to report the rates of increase in an even-handed manner. As the Table shows, tampon pledgets of the present disclosure exhibit a rate increase that is statistically significantly higher than existing commercial offerings. Notably, the average positive displacement rate is greater than 0.145. Preferably, the average displacement rate is greater than about 0.2.

TABLE 1

Positive Displacement Results for Various Super Absorbency Tampons

| Example | Manufacturer | Positive Displacement Rate (ml increase per minute weight of pledget, ml (g - | | Average % relative to that for Example 7 |
|---|---|---|---|---|
| | | Average | Standard Deviation | |
| Comparative 4 | Procter & Gamble | 0.073 | 0.021 | 36.3% |
| Comparative 5 | Procter & Gamble | 0.141 | 0.048 | 69.7% |
| Comparative 6 | Kimberly-Clark | 0.064 | 0.015 | 31.6% |
| Example 7 | Present Invention | 0.202 | 0.034 | 100.0% |

The tampon pledgets according to the present disclosure, as exemplified by Example 7 in Table 1, have the majority of the absorption potential near the bottom of the tampon pledget. As a result of arranging the absorbent material of each tampon pledget in such a manner it promotes an expansion of the pledget that reduces bypass leakage.

The positive displacement in vitro test suggests that tampon pledgets of the present disclosure expand more rapidly than tampon pledgets made by alternative means. Moreover, the observed shapes that these tampon pledgets take during expansion (see Figures), owing to the modified weight and area distributions together with in vivo results suggests that tampon pledgets of the present disclosure should be more suitable "plugs" and thus provide more effective bypass leakage prevention.

While the present disclosure has been described with reference to one or more exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the scope thereof.

The invention claimed is:

1. A process for assembling a tampon, comprising the following steps:
   forming one or more bottom pads from a first web of material such that the one or more bottom pads have a length dimension of between about 1 inches and about 4 inches and a width dimension of about 2 inches;
   forming one or more top pads from a second web of material;
   arranging the one or more top pads and the one or more bottom pads in a crosspad configuration such that a fiber distribution ratio of the one or more top pads and the one or more bottom pads is about 1:1;
   folding the crosspad configuration;
   forming a cylindrical shaped tampon pledget using a first ram to deliver the crosspad configuration into a cylindrical shaped transfer tube;
   transferring the cylindrical shaped tampon pledget by a second ram into an oven tube;
   transferring the cylindrical shaped tampon pledget into a stringer tube having a stringer tube diameter sized to permit a needle to enter the stringer tube;
   piercing the cylindrical shaped tampon pledget with a needle to permit a string to be added and tied;
   adding the cylindrical shaped tampon pledget to a plastic applicator; and forming closed petals on the plastic applicator to close the petals to enclose the pledget within the plastic applicator.

2. The process of assembling a tampon according to claim 1, wherein one of the one or more bottom pads and one or more top pads has a moisture level, as measured by a Halogen Moisture analyzer, of about 9.78%.

3. The process for assembling a tampon according to claim 2, wherein the other of the one or more bottom pads and one or more top pads has a moisture level, as measured by a Halogen Moisture analyzer, of about 11.55%.

4. The process for assembling a tampon according to claim 1, wherein the folding includes the use of the first ram having a dimension of about 0.25 inches.

5. The process for assembling a tampon according to claim 4, wherein the first ram is fluted.

6. The process for assembling a tampon according to claim 1, wherein the oven tube is heated to a temperature of about 220 degrees Fahrenheit.

7. The process for assembling a tampon according to claim 6, wherein the heating of the cylindrically shaped tampon pledget within the oven tube includes moving the oven tube through a conveyor oven.

8. The process for assembling a tampon according to claim 7, wherein the conveyor oven is a preheated IR conveyor oven.

9. The process for making a tampon pledget according to claim 1, wherein the first web for the one or more bottom pads has a different fiber than the second web for the one or more top pads.

10. The process for assembling a tampon according to claim 1, wherein the cylindrical shaped tampon pledget has an average positive displacement rate that is greater than about 0.2 ml/min/gram.

11. The process for assembling a tampon according to claim wherein the forming the petals is done by heating the petals and shaping the petals while heated.

12. A process for assembling a tampon having an absorbency in the super absorbency range of 9 grams to 12 grams, comprising:
 forming a bottom pad from a first web of absorbent material such that the bottom pad has a length dimension of in the range from about 1 inches to about 4 inches and a width dimension of about 2 inches;
 forming a top pad from a second web of absorbent material such that the top pad has a length dimension of about 4 inches and a width dimension of about 2 inches;
 arranging the top pad and the bottom pad in a crosspad configuration such that a fiber weight distribution ratio of the top pad to the bottom pad is about 1:1;
 folding the crosspad configuration;
 compressing the folded crosspad configuration into a cylindrically shaped tampon pledget;
 transferring the cylindrically shaped tampon pledget into an oven tube having an inside diameter of about 0.5 inches;
 heating the cylindrically shaped tampon pledget within the oven tube;
 piercing a bottom end of the cylindrically shaped tampon pledget with a needle to permit a string to be added and tied;
 adding the cylindrical shaped tampon pledget to a plastic applicator having petals on an end thereof, the cylindrical shaped tampon pledget having a total weight of about 2.6 grams and a greater absorption potential near the bottom of the cylindrically shaped tampon pledget; and
 after the adding, forming the petals on the plastic applicator to close the petals to enclose the pledget within the plastic applicator.

13. The process of assembling a tampon according to claim 12, wherein one of the bottom pad or the top pad has a moisture level, as measured by a Halogen Moisture analyzer, of about 9.78%.

14. The process for assembling a tampon according to claim 13, wherein the other of the bottom pad or the top pad has a moisture level, as measured by a Halogen Moisture analyzer, of about 11.55%.

15. The process for assembling a tampon according to claim 12, wherein the folding and compressing include the use of a ram having a dimension of about 0.25 inches.

16. The process for assembling a tampon according to claim 15, wherein the ram is fluted.

17. The process for assembling a tampon according to claim 12, wherein the oven tube is heated to a temperature of about 220 degrees Fahrenheit.

18. The process for assembling a tampon according to claim 12, wherein the heating of the cylindrically shaped tampon pledget within the oven tube includes moving the oven tube through a conveyor oven.

19. The process for assembling a tampon according to claim 18, wherein the conveyor oven is a preheated IR conveyor oven.

20. The process for making a tampon pledget according to claim 12, wherein the first web for the bottom pad has a different fiber than the second web for the to pad.

21. The process for assembling a tampon according to claim 12, wherein the cylindrical shaped tampon pledget has an average positive displacement rate that is greater than about 0.2 ml/min/gram.

22. The process for assembling a tampon according to claim 12, wherein the forming the petals is done by heating the petals and shaping the petals while heated.

23. A process for assembling a tampon, comprising the following steps:
 forming one or more bottom pads from a first web of material;
 forming one or more top pads from a second web of material;
 arranging the one or more top pads and the one or more bottom pads in a crosspad configuration such that a fiber distribution ratio of the one or more top pads and the one or more bottom pads is about 1:1;
 folding the crosspad configuration;
 forming a shaped tampon pledget using a first ram to deliver the crosspad configuration into a cylindrical shaped transfer tube, wherein the tampon pledget has an insertion tip region having an insertion tip end and an insertion rearward end, a main body region having a main forward end and a main rearward end, and a withdrawal region having a withdrawal forward end and withdrawal rearward end, the insertion rearward end is adjacent the main forward end, and the main rearward end is adjacent the withdrawal forward end, wherein the shaped tampon pledget is formed by the first ram into the transfer tube such that the shaped tampon pledget has a maximum diameter of the insertion tip region and the main body region where the insertion rearward end and the main forward end meet, wherein the main body region tapers from the maximum diameter to a minimum diameter and thereafter increases to a middle diameter that is greater than the minimum diameter;

transferring the shaped tampon pledget by a second ram into an oven tube;

transferring the shaped tampon pledget into a stringer tube having a stringer tube diameter sized to permit a needle to enter the stringer tube;

piercing the shaped tampon pledget with a needle to permit a string to be added and tied;

adding the shaped tampon pledget to a plastic applicator; and forming petals on the plastic applicator to close the petals to enclose the pledget within the plastic applicator.

24. The process of assembling a tampon according to claim 23, wherein one of the one or more bottom pads and the one or more top pads has a moisture level, as measured by a Halogen Moisture analyzer, of about 9.78%.

25. The process for assembling a tampon according to claim 24, wherein the other of the one or more bottom pads and the one or more top pads has a moisture level, as measured by a Halogen Moisture analyzer, of about 11.55%.

26. The process for assembling a tampon according to claim 23, wherein the folding and forming includes the use of the first ram having a dimension of about 0.25 inches.

27. The process for assembling a tampon according to claim 26, wherein the first ram is fluted.

28. The process for assembling a tampon according to claim 23, wherein the oven tube has an inside diameter of about 0.5 inches.

29. The process for assembling a tampon according to claim 23, wherein the oven tube is heated to a temperature of about 220 degrees Fahrenheit.

30. The process for assembling a tampon according to claim 23, wherein the oven tube is a heated oven tube and includes moving the oven tube through a conveyor oven.

31. The process for assembling a tampon according to claim 30, wherein the conveyor oven is a preheated IR conveyor oven.

32. The process for making a tampon pledget according to claim 23, wherein the first web for the one or more bottom pads is different from the second web for the one or more top pads.

33. The process for assembling a tampon according to claim 23, wherein the shaped tampon pledget has an average positive displacement rate that is greater than about 0.2 ml/min/gram.

34. The process for assembling a tampon according to claim 23, wherein the forming the petals is done by heating the petals and shaping the petals while heated.

35. The process of assembling a tampon according to claim 23, wherein the one or more bottom pad has a length dimension in the range from about 1 inches to about 4 inches and a width dimension of about 2 inches.

36. The process of assembling a tampon according to claim 23, wherein the one or more top pads has a length dimension of about 4 inches and a width dimension of about 2 inches.

37. The process of assembling a tampon according to claim 23, wherein the shaped tampon pledget having a total weight of about 2.6 grams.

38. The process of assembling a tampon according to claim 23, wherein the shaped tampon pledget has a greater absorption potential near a bottom of the shaped tampon pledget.

* * * * *